(12) United States Patent
Zollinger et al.

(10) Patent No.: US 9,370,651 B2
(45) Date of Patent: Jun. 21, 2016

(54) NEEDLELESS CONNECTOR WITH REDUCED TRAPPED VOLUME

(71) Applicant: CareFusion 303, Inc., San Diego, CA (US)

(72) Inventors: Christopher J. Zollinger, Chino Hills, CA (US); George Michel Mansour, Pomona, CA (US); Tyler Devin Panian, Long Beach, CA (US); Jonathan Yeh, Diamond Bar, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 13/801,422

(22) Filed: Mar. 13, 2013

(65) Prior Publication Data
US 2014/0276460 A1    Sep. 18, 2014

(51) Int. Cl.
*A61M 39/22* (2006.01)
*A61M 39/26* (2006.01)

(52) U.S. Cl.
CPC ............... *A61M 39/22* (2013.01); *A61M 39/26* (2013.01)

(58) Field of Classification Search
CPC ..... A61M 39/10; A61M 39/16; A61M 39/22; A61M 2039/24; A61M 39/2433; A61M 39/24332
USPC .......... 604/533, 249, 256, 246, 247; 251/319, 251/324, 325, 149.1, 149.6
See application file for complete search history.

(56) References Cited

U.S. PATENT DOCUMENTS

| | | |
|---|---|---|
| 4,141,379 A | 2/1979 | Manske |
| 4,535,820 A | 8/1985 | Raines |
| 4,654,031 A | 3/1987 | Lentz |
| 4,911,403 A | 3/1990 | Lockwood, Jr. |
| 5,092,857 A | 3/1992 | Fleischhacker |
| 5,555,908 A | 9/1996 | Edwards et al. |
| 5,623,969 A | 4/1997 | Raines |
| 5,690,612 A | 11/1997 | Lopez et al. |

(Continued)

FOREIGN PATENT DOCUMENTS

| | | |
|---|---|---|
| CN | 1139010 A | 1/1997 |
| EP | 2075032 A1 | 7/2009 |

(Continued)

OTHER PUBLICATIONS

Extended European Search Report in European Application No. 14158885.5 dated May 12, 2014.

(Continued)

*Primary Examiner* — Kami A Bosworth
*Assistant Examiner* — Hamza Darb
(74) *Attorney, Agent, or Firm* — McDermott Will & Emery LLP

(57) ABSTRACT

A female connector has a body with an internal cavity having a port and an internal surface. A collapsible valve is disposed within the internal cavity. The valve has a head with an external surface, wherein the head is in sealing contact with the internal surface of the internal cavity at a first location separated from the port so as to create a primary seal and at a second location proximate to the port so as to form a secondary seal when the female connector is not mated with a compatible male connector. The valve also has a neck coupled to the head proximal to the primary seal. The neck has a smiley cut. The valve also has a base portion coupled to the neck proximal to the smiley cut.

23 Claims, 4 Drawing Sheets

(56) References Cited

U.S. PATENT DOCUMENTS

| | | | |
|---|---|---|---|
| 5,699,821 A * | 12/1997 | Paradis | 137/1 |
| 5,730,418 A | 3/1998 | Feith et al. | |
| 5,782,816 A | 7/1998 | Werschmidt et al. | |
| 5,992,462 A | 11/1999 | Atkinson et al. | |
| 6,024,729 A | 2/2000 | Dehdashtian et al. | |
| 6,050,978 A | 4/2000 | Orr et al. | |
| 6,245,048 B1 | 6/2001 | Fangrow, Jr. et al. | |
| 6,679,219 B1 | 1/2004 | Pacinelli | |
| 6,886,803 B2 | 5/2005 | Mikiya et al. | |
| 7,184,825 B2 | 2/2007 | Leinsing et al. | |
| 8,291,936 B2 | 10/2012 | Carmody et al. | |
| 8,568,371 B2 | 10/2013 | Siopes et al. | |
| 2002/0193752 A1 | 12/2002 | Lynn | |
| 2003/0050610 A1 | 3/2003 | Newton et al. | |
| 2003/0098430 A1 | 5/2003 | Leinsing et al. | |
| 2005/0059952 A1 | 3/2005 | Giuliano et al. | |
| 2005/0222541 A1 | 10/2005 | Lopez et al. | |
| 2006/0025724 A1 | 2/2006 | Chen | |
| 2006/0027270 A1 * | 2/2006 | Truitt et al. | 137/843 |
| 2006/0089603 A1 | 4/2006 | Truitt et al. | |
| 2006/0163515 A1 | 7/2006 | Ruschke | |
| 2007/0270756 A1 | 11/2007 | Peppel et al. | |
| 2008/0108956 A1 | 5/2008 | Lynn et al. | |
| 2009/0030401 A1 | 1/2009 | Phillips | |
| 2009/0057589 A1 | 3/2009 | Thorne, Jr. et al. | |
| 2009/0299300 A1 | 12/2009 | Truitt et al. | |
| 2010/0036330 A1 | 2/2010 | Plishka et al. | |
| 2010/0256573 A1 | 10/2010 | Mansour et al. | |
| 2011/0028914 A1 | 2/2011 | Mansour et al. | |
| 2011/0028915 A1 | 2/2011 | Siopes et al. | |
| 2011/0046573 A1 | 2/2011 | Newton et al. | |
| 2011/0130724 A1 | 6/2011 | Mansour et al. | |
| 2011/0152787 A1 | 6/2011 | Truitt et al. | |
| 2012/0310179 A1 | 12/2012 | Truitt et al. | |
| 2012/0316514 A1 | 12/2012 | Mansour | |
| 2013/0190684 A1 * | 7/2013 | Panian et al. | 604/68 |

FOREIGN PATENT DOCUMENTS

| | | |
|---|---|---|
| EP | 2719419 A1 | 4/2014 |
| WO | 98/26835 A1 | 6/1998 |
| WO | WO-2004082756 A1 | 9/2004 |
| WO | WO-2004/112866 A2 | 12/2004 |
| WO | WO-2006078355 A1 | 7/2006 |
| WO | WO-2008091698 A2 | 7/2008 |
| WO | WO-2011014265 A1 | 2/2011 |
| WO | WO-2011060384 A1 | 5/2011 |
| WO | WO-2013016077 A2 | 1/2013 |
| WO | WO-2013099261 A1 | 7/2013 |
| WO | WO-2013122148 A1 | 8/2013 |

OTHER PUBLICATIONS

International Search Report and Written Opinion in PCT Application No. PCT/US2014/017824 mailed May 9, 2014.
International Search Report and Written Opinion in PCT Application No. PCT/US2014/017826 mailed May 8, 2014.
International Search Report and Written Opinion in PCT Application No. PCT/US2014/017828 mailed May 2, 2014.
Extended European Search Report in European Application No. 14158882.2 dated Jul. 7, 2014, 7 pages.
Extended European Search Report in European Application No. 14158891.3 dated Jul. 8, 2014, 6 pages.
Extended European Search Report in European Application No. 14158899.6 dated Jul. 8, 2014, 6 pages.
International Search Report and Written Opinion in International Application No. PCT/US2014/017486 mailed May 13, 2014, 14 pages.
International Search Report and Written Opinion in International Application No. PCT/US2014/023694 mailed Jun. 26, 2014, 11 pages.
International Written Opinion of the International Preliminary Examining Authority for International Application No. PCT/US2014/017828, dated Mar. 20, 2015, 6 pages.
International Written Opinion of the International Preliminary Examining Authority for International Application No. PCT/US2014/017824, dated Mar. 23, 2015, 6 pages.
European Office Action for Application No. 14158894.7, dated Dec. 16, 2015, 5 pages.
Extended European Search Report; Application No. 14158894.7, dated May 12, 2014.
International Search Report and Written Opinion for PCT Application No. PCT/US2014/017480 dated May 13, 2014.
European Office Action for Application No. 14158885.5, dated Dec. 16, 2015, 5 pages.

* cited by examiner (area B)
PRIOR ART

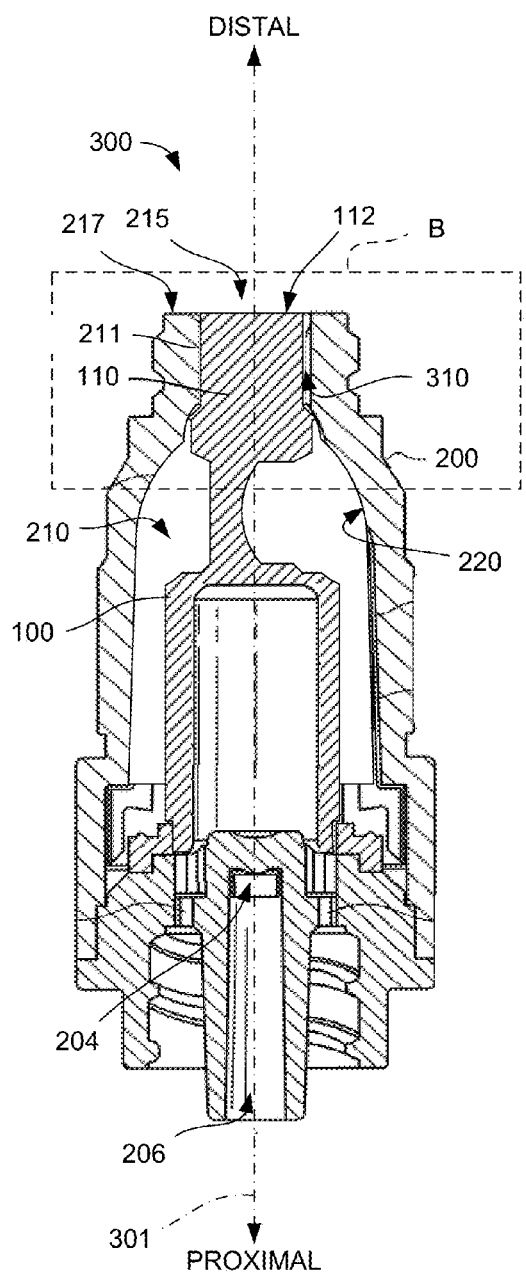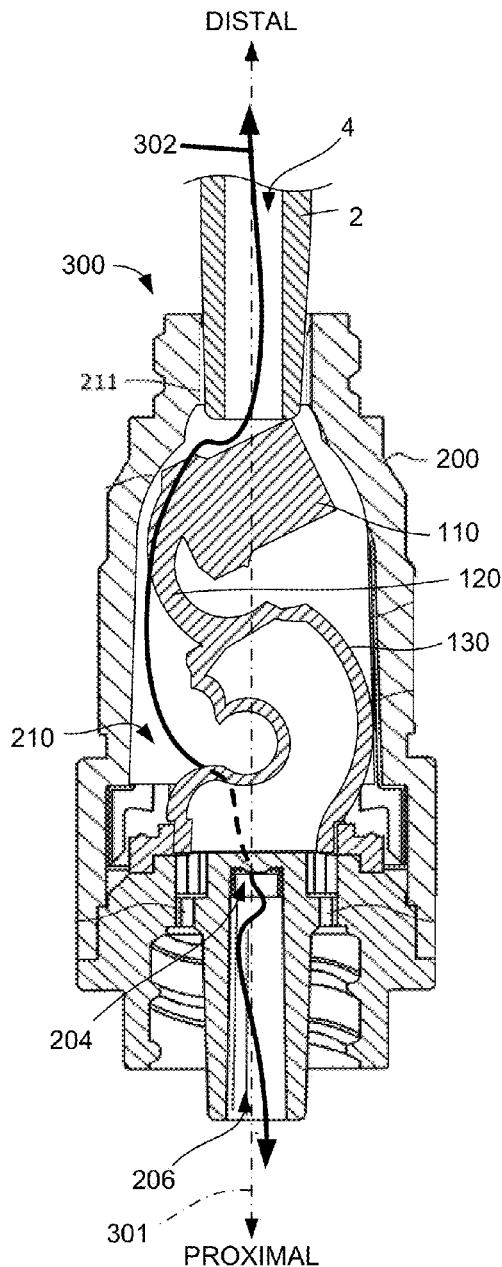
FIG. 3
FIG. 4

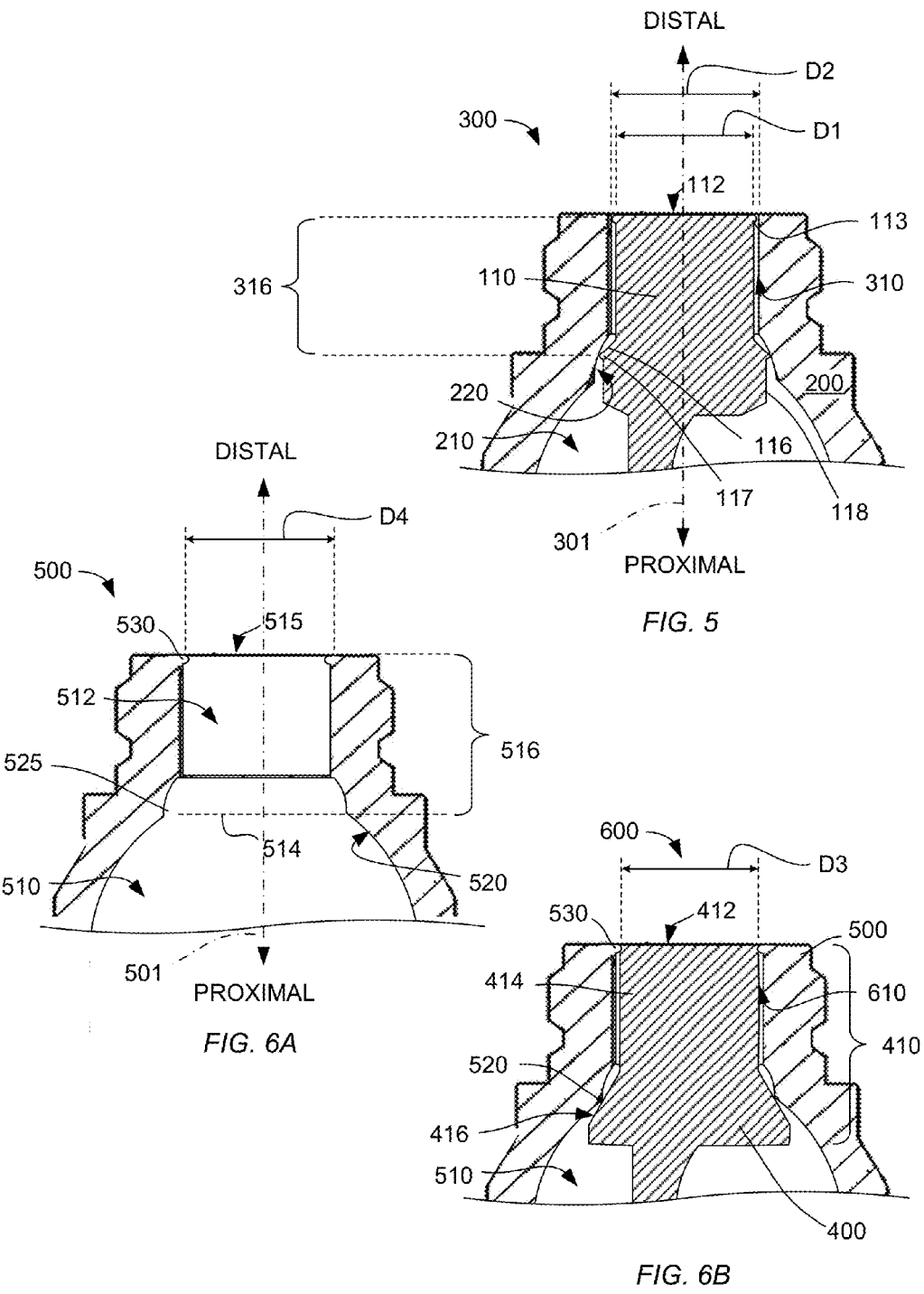

NEEDLELESS CONNECTOR WITH REDUCED TRAPPED VOLUME

CROSS-REFERENCES TO RELATED APPLICATIONS

Not applicable.

BACKGROUND

1. Field

The present disclosure generally relates to needleless connectors, and, in particular, to connectors with an internal collapsible valve.

2. Description of the Related Art

Medical treatments often include the infusion of a medical fluid, for example a saline solution or a liquid medication, to patients using an intravenous (IV) catheter that is connected though an arrangement of flexible tubing and fittings, commonly referred to as an "IV set," to a source of fluid, for example an IV bag. The fittings commonly include interconnectable male and female needleless connectors having a "Luer taper" conforming to an International Standards Organization (ISO) standard, although certain needleless connectors may not have Luer tapers. Certain connectors have a self-sealing feature to prevent leakage of fluid from the attached tubing when the connector is decoupled from a mating connector.

FIG. 1A depicts a conventional needleless connector 10 with a collapsible internal valve 20 made of a flexible material. When a force is applied to the top 24 of the valve 20 by the tip of a male Luer connector (not shown), the valve folds at a "smiley cut" 26 located in the upper portion 22, referred to as the "head" of the valve, thereby opening a flow path through the connector 10. In the closed position shown in FIG. 1A, a primary seal is formed between a shoulder 30 of the valve 20 and a sealing ridge 54 of the body 50 and a secondary seal is formed between the rim around the external surface 24 of the valve 20 and the edge of the port 52 of the body 50. Between the primary and secondary seals and between the body 50 and the valve 20, a volume 53 is formed that contains trapped liquid when the connector 10 is demated from a previously connected male Luer connector. In certain circumstances, it is desirable to minimize volume 53.

SUMMARY

The self-sealing female needleless connector disclosed herein has a reduced internal volume compared to conventional connectors of the same type and, therefore, may trap a reduced amount of fluid within the connector upon disconnection.

In certain embodiments, a female connector is disclosed that includes a body comprising an internal cavity having a port and an internal surface and a collapsible valve disposed within the internal cavity. The valve has a head comprising an external surface, wherein the head is in sealing contact with the internal surface of the internal cavity at a first location separated from the port so as to create a primary seal and at a second location proximate to the port so as to form a secondary seal when the female connector is not mated with a compatible male connector. The valve also has a neck coupled to the head proximal to the primary seal, the neck comprising a smiley cut. The valve also has a base portion coupled to the neck proximal to the smiley cut.

In certain embodiments, a connector is disclosed that includes a body comprising an internal cavity having a port and a collapsible valve disposed within the internal cavity. The valve has distal and proximal ends and a head comprising an external surface disposed at a distal end and a ridge that is proximal to and separated from the external surface. The valve also has a neck coupled to the head proximal to the ridge, the neck comprising a smiley cut, and a base portion coupled to the neck proximal to the smiley cut. The ridge of the valve is in sealing contact with the body so as to form a primary seal when the connector is not mated with a compatible connector.

In certain embodiments, a female connector is disclosed that includes a body having distal and proximal ends and comprising an internal cavity with an internal surface, a port at a distal end of the internal cavity, and a ridge formed on the internal surface. The ridge is proximal to and separated from the port. The connector also includes a collapsible valve disposed within the internal cavity. The valve has distal and proximal ends and a head comprising an external surface disposed at a distal end and a shoulder proximal to and separated from the external surface. The valve also has a neck coupled to the head proximal to the shoulder. The neck has a smiley cut. The valve also has a base portion coupled to the neck proximal to the smiley cut. The ridge of the body is in sealing contact with the shoulder so as to create a primary seal when the female connector is not mated with a compatible connector.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 3-4 are cross-sections of an exemplary needleless connector that includes the valve of FIG. 2 according to certain aspects of the present disclosure.

FIG. 5 is an enlarged view of a portion of the needleless connector of FIG. 3 according to certain aspects of the present disclosure.

FIGS. 6A-6B are enlarged views of a portion of another embodiment of a needleless connector according to certain aspects of the present disclosure.

DETAILED DESCRIPTION

It is advantageous to provide a self-sealing, needleless connector that accepts male Luer fittings that meet the ISO standard while the size of the connector, and therefore the volume of fluid within the connector, is reduced compared to conventional connectors.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. In the referenced drawings, like numbered elements are the same or essentially similar. Reference numbers may have letter suffixes appended to indicate separate instances of a common element while being referred to generically by the same number without a suffix letter.

Figures 1A, 1B:
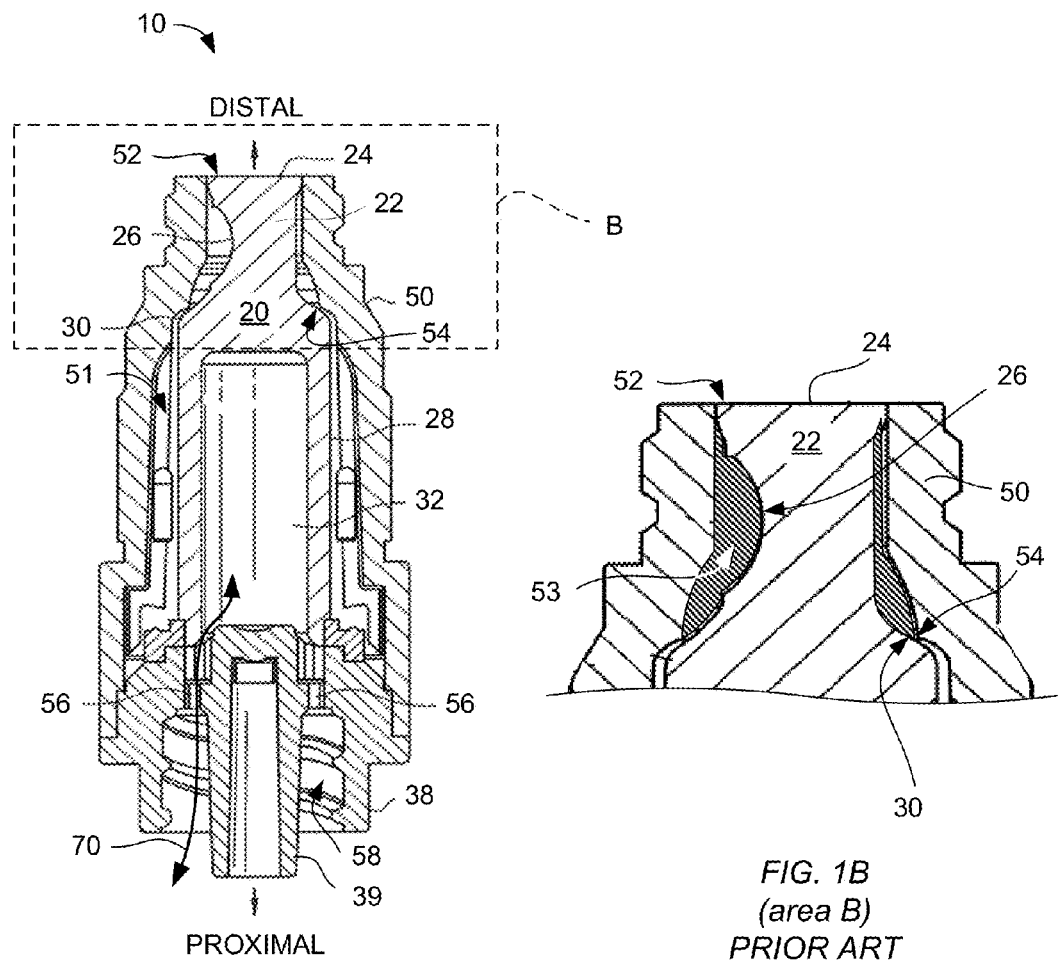
FIGS. 1A-1B are cross-sections of a conventional needleless connector.

FIGS. 1A-1B are cross-sections of a conventional needleless connector 10. With reference to FIG. 1A, the connector 10 includes a collapsible valve 20 disposed within a internal cavity 51 of body 50. The valve 20 has a shoulder 30 that continuously contacts a ridge 54 within the internal cavity 51 when the connector 10 is de-activated, i.e. not connected to a mating connector, to form a primary seal that blocks the fluid flow path through the connector 10. The valve 20 has an internal air space 32 that is separated from the internal cavity 51 by a cylindrical wall 28. The air space 32 is vented to the ambient environment through air passages 56 and the external cavity 58 within the threaded connector 38 surrounding the male Luer fitting 39 of the body 50, as indicated by the air flow path 70. The valve 20 also has a solid head 22 with a "smiley cut" 26 formed on one side and a external surface 24 that is positioned generally flush with a port 52 of the internal cavity 51 when the connector 10 is de-activated. The external surface 24 is continuous, i.e. there is no slit or penetration in the surface that may trap bacteria or other contamination. The edge of the external surface 24 seals to the port 52 to form a secondary seal.

FIG. 1B depicts an enlarged portion of FIG. 1 defined by the dashed-line box labeled "B." The portion of internal cavity 51 that is between the primary and secondary seals, and external to the valve 20, is a trapped volume 53 that encircles the head 22 and fills the smiley cut 26.

Figure 2:
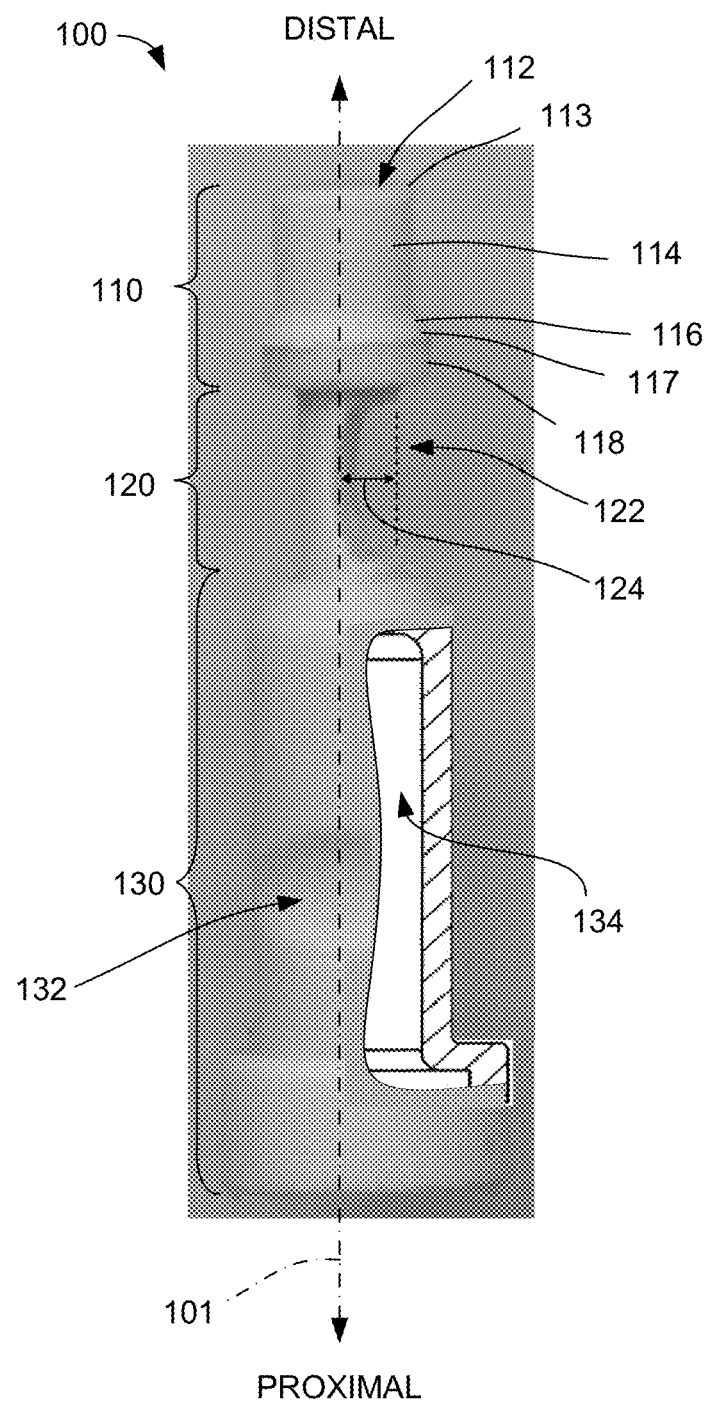
FIG. 2 is a perspective view of an exemplary internal valve for a needleless connector according to certain aspects of the present disclosure.

FIG. 2 is a perspective view of an exemplary internal valve 100 for a needleless connector according to certain aspects of the present disclosure. The valve 100 has a head 110, a neck 120, and a base portion 130 arranged along a distal-proximal axis 101. As shown in FIG. 2, the head 110 comprises an external surface 112 and a shoulder 116 that is proximal to the external surface 112. The neck 120 is coupled to the head 110 proximal to the shoulder 116 and comprises a smiley cut 122. The base portion 130 is coupled to the neck 120 proximal to the smiley cut 122. In certain embodiments, the valve 100 is formed as a single piece while, in other embodiments, the valve 100 may be formed by coupling two or more elements, for example by adhesive bonding. In certain embodiments, the valve 100 comprises an elastomeric material, for example a silicone. In certain embodiments, the valve 100 may comprise rigid or semi-rigid materials, for example a polyethylene.

In this example, the base portion 130 has an external dimple 132 and an internal volume 134, visible in the cutaway portion of the base portion 130, that is open at the proximal end of the base portion 130. The dimple 132 controls the collapse of the base portion 130 under a compressive load when the connector 10 is actuated as shown in FIG. 4.

The neck 120 has a smiley cut 122 that is, in this example, approximately half the thickness of the neck 120. The smiley cut 122 controls how the neck 120 folds under the same compressive load, as shown in FIG. 4. The smiley cut 122 has a depth 124 measured as the maximum distance from the curved surface of the smiley cut 122 to a reference feature defined by a continuation of the cylindrical surface of the neck 120 over the smiley cut 122. In certain embodiments, the smiley cut 122 has a constant profile across the cut while, in other embodiments, the smiley cut 122 may have curvature perpendicular to the distal-proximal axis 101. In certain embodiments, the smiley cut 122 is symmetric while, in other embodiments, the smiley cut 122 may have a non-symmetric profile. In certain embodiments, the smiley cut 122 has the form of a continuous curve while, in other embodiments, the smiley cut 122 may have corners and/or flat surfaces.

The head 110 comprises a cylindrical portion 114 and an extended portion 118, with the shoulder 116 disposed between the portions 114 and 118. In certain embodiments, the head 110 is solid while, in other embodiments, the head 110 may have an internal recess (not visible in FIG. 2).

The shoulder 116, in this example, extends outward at an angle from the cylindrical portion 114 in a proximal direction. In certain embodiments, the angle of the shoulder 116 is in the range of 15-75°. In certain embodiments, the angle is in the range of 30-60°. In certain embodiments, the angle is approximately 40°.

In certain embodiments, there is a raised ridge 113 formed around the head 110 at the edge of the external surface 112. In certain embodiments, there is a raised ridge 117 formed around the head 110 at the interface between the shoulder 116 and extension portion 118. The ridges 113 and 117 are discussed in greater detail with respect to FIG. 5.

FIGS. 3-4 are cross-sections of an exemplary needleless connector 300 that includes the valve 100 of FIG. 2 according to certain aspects of the present disclosure. The connector 300 is defined as a "female" valve that is configured to separably mate with a compatible "male" connector (not shown in FIG. 3). FIG. 3 depicts the connector 300 in a first configuration wherein the connector 300 is not mated with a compatible male connector. The connector 300 has a distal-proximal axis 301 and, in certain embodiments, the connector 300 is generally symmetric about the axis 301.

The connector 300 comprises a body 200 with an internal cavity 210 having a port 215 disposed, in this example, at a distal end of the body 200. The internal cavity 210 has an internal surface 220. The body 200 includes an output flow channel 206 that is, in this example disposed at the proximal end. A passage 204 connects the internal cavity 210 to the output flow channel 206 in a plane that is perpendicular to the plane of the cross-section in FIG. 3.

The valve 100 is disposed within the internal cavity 210 with the external surface 112 approximately flush with the surface 217 that surrounds the port 215. The head 110 is disposed within a cylindrical portion 211 of the internal cavity 210 that is proximate to the port 215 so as to form a trapped volume 310. The details of this region of connector 300 are discussed in greater detail with respect to FIG. 5.

FIG. 4 depicts the connector 300 in a second configuration wherein the connector 300 is mated with a compatible male connector having a male fitting 2 with an internal flow passage 4. The fitting 2 has been inserted through port 215 into cylindrical portion 211 of the internal cavity 210, thereby displacing the head 110 of valve 100 and applying a compressive load to the head 110 in a proximal direction along the distal-proximal axis 301. The compressive load is transferred through the neck 120 and base portion 130 to the body 200, causing the neck 120 to fold and the base portion 130 to collapse generally as depicted in FIG. 4. The deformed configuration of valve 100 is only illustrative and other deformed positions of the valve 100 are within the scope of this disclosure. Once the fitting 2 is fully mated with the connector 300, a fluid flow path 302 is opened from the internal flow passage 4 through the internal cavity 210 around the collapsed valve 100 and through passage 204 to the output flow channel 206.

FIG. 5 is an enlarged view of a portion of the needleless connector 300 of FIG. 3 according to certain aspects of the present disclosure. In this enlarged view, the ridge 113 formed around the edge of the external surface 112 and the ridge 117 formed at the juncture of the shoulder 116 and extended portion 118 are visible. When the connector 300 is in the first configuration of FIG. 3, the ridge 117 is in sealing contact with the surface 220 of the internal cavity 210, thereby forming a primary seal that blocks the fluid flow path 302. At the same time, while connector 300 is in the first configuration, the ridge 113 is in sealing contact with the body 200, thereby forming a secondary seal that also blocks the fluid flow path 302 as well as preventing any liquid within the internal cavity 210 from leaking from the port 215 after a male connector is removed. A trapped volume 310 is formed within the internal cavity 210 and defined as the volume bounded by the primary and secondary seals, the head 110, and the body 200.

In certain embodiments, the head 110 has a diameter D1, excluding the ridge 113. In certain embodiments, D1 is less than or equal to 0.20 inch. In certain embodiments, D1 is approximately equal to 0.17 inch. In certain embodiments, the cylindrical portion 211 has a diameter D2 that is greater than D1 by a difference that is less than or equal to 0.010 inch. In certain embodiments, the ridges 113 and 117 are separated along the distal-proximal axis 301 by a distance 316 that is less than or equal to 0.10 inch. In certain embodiments, the trapped volume 310 is less than or equal to 0.00004 cubic inch.

FIGS. 6A-6B are enlarged views of a portion of another embodiment 600 of a needleless connector according to certain aspects of the present disclosure. FIG. 6A depicts a body 500 that forms part of connector 600. The body 500 has an internal cavity 510 with a cylindrical portion 512 disposed proximate to a port 515 having a surrounding surface 530. A ridge 525 is formed on the surface 220 of the cavity 510. In certain embodiments, the ridge 525 lies in a plane 514 that is perpendicular to a distal-proximal axis 501. The body 500 comprises a ridge 530 formed around the port 515 and protruding into the cylindrical portion 512.

FIG. 6B depicts a valve 400 disposed within the body 500 of FIG. 5 to form a connector 600. The valve 400 is generally similar to valve 100, having a head 410 with an external surface 412, a cylindrical portion 414, and a shoulder 416, except that valve 400 lacks the ridges 113 and 117 of valve 100. When connector 600 is in a configuration wherein the connector 300 is not mated with a compatible male connector, the external surface 412 of valve 400 is approximately flush with the port 515 and the shoulder 416 is in sealing contact with the ridge 525 to form a primary seal and ridge 530 is in sealing contact with the head 414 to form a secondary seal. The space within the internal cavity 510 between the primary and secondary seals, the head 410, and body 500 forms the trapped volume 610.

In certain embodiments, the head 410 has a diameter D3. In certain embodiments, D3 is less than or equal to 0.20 inch. In certain embodiments, D3 is approximately equal to 0.17 inch. In certain embodiments, the cylindrical portion 512 has a diameter D4 that is greater than D3 by a difference that is less than or equal to 0.050 inch. In certain embodiments, the ridges 525 and 530 are separated along the distal-proximal axis 301 by a distance 516 that is less than or equal to 0.20 inch. In certain embodiments, the trapped volume 610 is less than or equal to 0.01 cubic inch.

In summary, the positioning of the primary seal distal to the smiley cut of valve provides a reduced volume of fluid trapped between the primary and secondary seals. This may reduce the amount of liquid that may leak past the secondary seal or improve the sealing performance due to the improved alignment of the primary and secondary seals.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but are to be accorded the full scope consistent with the claim language.

Reference in the claims or specification to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa.

Headings and subheadings, if any, are used for convenience only and do not limit the disclosure.

It is understood that the specific order or hierarchy of steps of methods disclosed in the specification is an illustration of exemplary approaches. Based upon design preferences, it is understood that the specific order or hierarchy of steps in the processes may be rearranged. Some of the steps may be performed simultaneously. Method claims present elements of the various steps in a sample order, and are not meant to be limited to the specific order or hierarchy presented.

Terms such as "top," "bottom," "front," "rear," and the like as used in this disclosure should be understood as relative references within an arbitrary frame of reference, rather than to the ordinary gravitational frame of reference. Thus, a top surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as "an aspect" may refer to one or more aspects. A term such as "embodiment" does not imply that such embodiment is essential to the subject technology or that such embodiment applies to all configurations of the subject technology. A disclosure relating to "an embodiment" may refer to one or more embodiments or to all embodiments.

The word "exemplary" is used herein to mean "serving as an example or illustration." Any aspect or design described herein as "exemplary" is not necessarily to be construed as preferred or advantageous over other aspects or designs.

The terms "include," "have," "with," and the like that are used in the claims or specification are intended to be inclusive in a manner similar to the manner in which "comprise" is interpreted when employed as a transitional word in a claim. No claim element is to be construed under the provisions of 35 U.S.C. §112, sixth paragraph, unless the element is expressly recited using the phrase "means for" or, in the case of a method claim, the element is recited using the phrase "step for."

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A female connector comprising:
 a body having distal and proximal ends and a distal-proximal axis, the body comprising an internal cavity having a port and an internal surface; and
 a collapsible valve disposed within the internal cavity, the valve comprising:

a head comprising an external surface and a shoulder, wherein the head is in sealing contact with the internal surface of the internal cavity at a first location separated from the port so as to create a primary seal at the shoulder and at a second location proximate to the port so as to form a secondary seal when the female connector is not mated with a compatible male connector, a cross-sectional width of the head at the shoulder being greater than a cross-section of the head at the second location;

a neck having a distal end and a proximal end, the distal end of the neck coupled to the head proximally of the primary seal, the neck comprising an outer surface having a smiley cut between the distal end and the proximal end of the neck, wherein when viewed in a cross-section, the neck (i) extends between the distal end and proximal end along only one side of the axis, and (ii) is radially spaced from the axis; and a base portion having a distal end and a proximal end, and an internal volume extending from the proximal end toward the distal end, the internal volume terminating at the distal end of the base, the proximal end of the neck extending distally from the distal end of the base portion.

2. The female connector of claim 1, wherein the body further comprises an output flow channel and a fluid flow path between the port and the output flow channel, and the primary seal and the secondary seal both block the fluid flow path when the connector is not mated with a compatible male connector.

3. The female connector of claim 1, wherein the head further comprises a ridge separated from the external surface and in sealing contact with the first location of the body to form the primary seal.

4. The female connector of claim 1, wherein the head further comprises a ridge formed around an edge of the external surface and in sealing contact with the second location of the body so as to form the secondary seal.

5. The female connector of claim 1, wherein:
the shoulder is separated from the external surface; and
the body further comprises a ridge that is formed on the internal surface of the internal cavity at the first location and in sealing contact with the shoulder so as to create the primary seal.

6. The female connector of claim 1, wherein the body further comprises a ridge formed on the internal surface of the internal cavity around the port and in sealing contact with the head to form the secondary seal.

7. The female connector of claim 1, wherein the internal cavity comprises a trapped volume bounded by the primary and secondary seals, the valve, and the internal surface of the internal cavity.

8. The female connector of claim 7, wherein the trapped volume is less than or equal to 0.01 cubic inch.

9. The female connector of claim 1, wherein the port and the first location are separated along the distal-proximal axis by a distance less than or equal to 0.20 inch.

10. The female connector of claim 9, wherein the port and the first location are separated by a distance less than or equal to 0.13 inch.

11. The female connector of claim 1, wherein the head comprises a cylindrical portion disposed between the external surface and the first location, the cylindrical portion of the head having a first diameter of less than or equal to 0.20 inch.

12. The female connector of claim 11, wherein the internal cavity comprises a cylindrical portion disposed between the port and the first location, the cylindrical portion of the internal cavity having a second diameter that is greater than the first diameter.

13. The female connector of claim 12, wherein the second diameter is greater than the first diameter by a difference that is less than or equal to 0.050 inch.

14. The female connector of claim 1, wherein the base portion comprises at least one dimple.

15. The female connector of claim 1, wherein:
the neck comprises a cylindrical portion having a diameter; and
the smiley cut has a depth that is greater than or equal to 30% of the diameter of the cylindrical portion.

16. The female connector of claim 15, the smiley cut has a depth that is greater than or equal to 50% of the diameter of the cylindrical portion.

17. The female connector of claim 1, wherein the external surface is substantially flush with the port when the female connector is not mated with a compatible male connector.

18. A connector comprising:
a body having distal and proximal ends and an axis between the distal and proximal ends, the body comprising an internal cavity having a port; and
a collapsible valve disposed within the internal cavity, the valve having distal and proximal ends and comprising:
a head comprising an external surface disposed at the distal end, a shoulder having ridge that is proximal to and separated from the external surface, and an edge that is proximate to the external surface to form a secondary seal, a ridge in sealing contact with the body to form a primary seal, and the edge in sealing contact with the body to form a secondary seal, a cross-sectional width of the head at the ridge being greater than a cross-sectional width of the head at the edge;
a neck having a distal end and a proximal end, the distal end of the neck coupled to the head proximally of the ridge, the neck comprising an outer surface having a smiley cut between the distal end and the proximal end of the neck, wherein when viewed in a cross-section, the neck (i) extends between the distal end and proximal end along only one side of the axis, and (ii) is radially spaced from the axis; and
a base portion having a distal end and a proximal end, and an internal volume extending from the proximal end toward the distal end, the internal volume terminating at the distal end of the base, the proximal end of the neck extending distally from the distal end of the base portion.

19. The connector of claim 18, wherein:
the external surface is substantially flush with the port when the connector is not mated with a compatible connector; and
the internal cavity comprises a trapped volume bounded by the primary and secondary seals, the valve, and the body.

20. The connector of claim 19, wherein the trapped volume is less than or equal to 0.01 cubic inch.

21. A female connector comprising:
a body having distal and proximal ends and an axis between the distal and proximal ends, the body comprising an internal cavity with an internal surface, a port at a distal end of the internal cavity, and a ridge formed on the internal surface, the ridge being proximal to and separated from the port; and
a collapsible valve disposed within the internal cavity, the valve having distal and proximal ends and comprising:

a head comprising an external surface disposed at a distal end, a first location proximal to and separated from the external surface, and a second location proximate to the port, a cross-sectional width of the head at the first location being greater than a cross-section of the head at the second location;

a neck having a distal end and a proximal end, the distal end of the neck coupled to the head proximally of the first location, the neck comprising an outer surface having a smiley cut between the distal end and the proximal end of the neck, wherein when viewed in a cross-section, the neck (i) extends between the distal end and proximal end along only one side of the axis, and (ii) is radially spaced from the axis; and a base portion having a distal end and a proximal end, and an internal volume extending from the proximal end toward the distal end, the internal volume terminating at the distal end of the base, the proximal end of the neck extending distally from the distal end of the base portion, wherein the ridge of the body is in sealing contact with the first location to create a primary seal, and the internal surface of the body is in sealing contact with the second location to create a secondary seal, when the female connector is not mated with a compatible connector.

22. The connector of claim 21, wherein:

the external surface is substantially flush with the port when the connector is not mated with a compatible connector; and the internal cavity comprises a trapped volume bounded by the primary and secondary seals, the valve, and the body.

23. The connector of claim 22, wherein the trapped volume is less than or equal to 0.01 cubic inch.

* * * * *